United States Patent [19]

Schubert et al.

[11] Patent Number: 4,490,278
[45] Date of Patent: Dec. 25, 1984

[54] LIQUID CRYSTAL SUBSTITUTED TRANS-4-N-ALKYLCYCLOHEXANES AND SUBST.-3-SUBST.-BENZOYLOXY-[TRANS-4-N-ALKYLCYCLOHEXANE]S

[76] Inventors: Herrmann Schubert, Dorfstrasse 9, DDR-4101 Nehlitz; Hans-Joachim Deutscher, Block 484-4, DDR-4090 Halle; Horst Kresse, Puschkinstrasse 18, DDR-4020 Halle; Dietrich Demus, Veilchenweg 22, DDR-4020 Halle; Heinz Altmann, Adolfstrasse 3, DDR-4020 Halle; Marlies Körber, Rolandweg 13, DDR-5500 Nordhausen; Ute Böttger, Röpziger Strasse 10, DDR-4020 Halle, all of German Democratic Rep.

[21] Appl. No.: 189,542

[22] Filed: Sep. 22, 1980

[30] Foreign Application Priority Data

Sep. 24, 1979 [DD] German Democratic Rep. ... 215742
Sep. 24, 1979 [DD] German Democratic Rep. ... 215743

[51] Int. Cl.³ .................... C09K 3/34; C07C 69/75; C07C 69/78; C07C 69/90; C07C 67/14
[52] U.S. Cl. ............... 252/299.63; 252/299.5; 350/350 R; 350/350 S; 560/1; 560/65; 560/73; 560/126
[58] Field of Search ......... 252/299.63, 299.5; 350/350 R, 350 S; 560/1, 116, 65, 118, 125, 73, 126

[56] References Cited

U.S. PATENT DOCUMENTS

| 4,130,502 | 12/1978 | Eidemschink et al. | 252/299.63 |
|---|---|---|---|
| 4,181,625 | 1/1980 | Eidemschink et al. | 252/299.63 |
| 4,229,315 | 10/1980 | Krause et al. | 252/299.63 |
| 4,293,434 | 10/1981 | Deutscher et al. | 252/299.63 |
| 4,349,452 | 9/1982 | Osman et al. | 252/299.61 |
| 4,368,135 | 1/1983 | Osman | 252/299.63 |
| 4,419,263 | 12/1983 | Praefcke et al. | 252/299.63 |

FOREIGN PATENT DOCUMENTS

| 23730 | 2/1981 | European Pat. Off. | 252/299.63 |
|---|---|---|---|
| 105701 | 5/1974 | German Democratic Rep. | 252/299.63 |
| 56-83449 | 7/1981 | Japan | 252/299.63 |
| 56-129287 | 10/1981 | Japan | 252/299.63 |
| 56-125318 | 10/1981 | Japan | 252/299.63 |
| 56-125342 | 10/1981 | Japan | 252/299.63 |
| 57-48945 | 3/1982 | Japan | 252/299.63 |
| 57-99557 | 6/1982 | Japan | 252/299.63 |

OTHER PUBLICATIONS

Osman; M. A., et al., Mol. Cryst. Liq. Cryst., vol. 56, (Letters); pp. 105–109, (1979).
Deutscher; H. J., et al., Advances in Liq. Cryst. Res. and Applications, Bata, L. Percamon Press, N.Y., N.Y., pp. 1075–1079, vol. 2, (1980), Proceedings of the Third Liquid Crystal Conference of the Socialist Countries, Budapest, 27–31, Aug. 1979.

Primary Examiner—Teddy S. Gron
Attorney, Agent, or Firm—Jordan and Hamburg

[57] ABSTRACT

The invention relates to liquid crystal nematic substances for electro-optical devices for the modulation of light, for the reproduction of numerals, signs and images as well as an orienting medium for spectroscopy and gas chromatography.

It was found that compounds containing two or three rings, connected by carboxyl groups are new liquid crystal nematic substances of the general formula

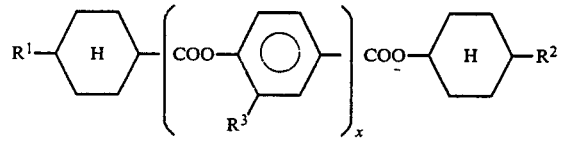

where $R^1 = C_nH_{2n+1}$, CN; $R^2 = C_mH_{2m+1}$, CN; $R^3 = H$, $CH_3$, $C_2H_5$ Cl, Br; x=0 or 1; m,n=numbers from 1 to 10 are suitable for electro-optical arrangements for the modulation of transmitted or reflected light as well as for the reproduction of numeral signals and images, and further, as an orienting medium for spectroscopy and gas chromotography.

Other liquid crystal substances or non-liquid crystalline substances, particularly dyes, may be added to the substances according to the invention.

9 Claims, No Drawings

LIQUID CRYSTAL SUBSTITUTED TRANS-4-N-ALKYLCYCLOHEXANES AND SUBST.-3-SUBST.-BENZOYLOXY-[TRANS-4-N-ALKYLCYCLOHEXANE]S

BACKGROUND OF THE INVENTION

The invention relates to liquid crystal nematic substances for electro-optical arrangements for modulation of light, for the reproduction of numbers, signs and images as well as to a method for their preparation.

It is known that various effects occuring in nematic crystalline liquids may be used for electro-optical arrangements (M. Tobias, International Handbook of Liquid Crystal Displays 1975-76, Ovum Ltd. London 1976). The orienting effect of liquid crystals may be exploited for investigations of anisotropic properties of added molecules. Furthermore, special separation effects may be obtained when liquid crystals are used as a stationary phase in gas chromatography (G. Meier, E. Sackmann, J. G. Grabmeier, Applications of Liquid Crystals, Springer Verlag, Berlin-Heidelberg-New York 1975).

A large number of substances are already known which, in principle, may be used for that purpose. (D. Demus in: Kmetz, Willisen: Non-emissive Electro-optic displays, Plenum Press New York 1976, page 4). Presently though, no substance is known whose properties in regard to melting and clarification temperature, dielectric anisotropy, viscosity and chemical stability, satisfy the parameters needed for practical application. In mixtures of substances, particularly eutectic mixtures, it is possible to extend to vastly lower temperatures the field of nematic existence by exploiting the depression of the melting point. In mixtures, furthermore, the parameters needed for electro-optical properties as dielectrical anisotropy, viscosity and double refraction, may be modified and adapted for the varying experimental needs. The condition, of course, is the presence of corresponding components of the mixture. The presently-known components do not exhibit optimal values in respect to the variability of the aforecited properties. The presently-known substituted benzoic acid phenylesters (DD WP 86 26 9; R. Stienstraesser, Z. Naturforsch. 27 b. 774 (1972)); substituted hydroquinone-bis-benzoates (DD WP 108 022 and 108 023); and substituted benzoyloxy-benzoic acid phenylester (Ang. Chem. 84, 636 (1972)) possess undesirably high viscosities, thereby causing disadvantageously high switching-on and -off periods in electro-optical arrangements, especially at low temperatures.

These disadvantages are partly reduced for 4-n-alkylcyclohexanecarboxylic acid-4-subst.-phenylesters (DD WP 105 701) as well as in compounds with a cyclohexane ring that contain three rings (DD WP C 09 K/197 331).

The need for additional components of mixtures still remains in order to be capable of obtaining desired properties by mixing thereof.

The objective of the invention is the creation of new liquid crystal nematic substances with advantageous properties in respect to melting and clarification point, dielectrical anisotropy and viscosity, for their use in electro-optical devices for the modulation of light as well as for the display of numbers, signs and designs and also to methods for their preparation.

The invention is based upon the task to obtain new classes of compounds with liquid-crystalline properties, suitable for practical use by starting with 2- or 3-ring esters respectively by exchanging benzene rings with cyclohexane rings.

SUMMARY OF THE INVENTION

It was found that compounds containing two to three rings, connected by carboxyl groups, represented new liquid-crystalline nematic substances of the following general formula

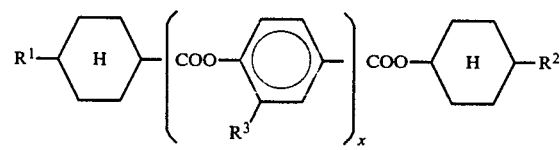

where $R^1 = C_nH_{2n+1}$, CN; $R^2 = C_mH_{2m+1}$, CN, $R^3 = H$, $CH_3$, $C_2H_5$, Cl, Br; $X = 0, 1$; $m, n = 1$ to 10. These compounds are suitable for modulation of transmitted light or reflected light, as well as for the reproduction of numbers, signals and images. The new substances are colorless, very stable against chemical influences, heat and irradiation by light. They possess positive dielectrical anisotropy, low viscosity and in connection with the aforedescribed properties, advantageous electro-optical properties.

The compounds where 1 equals 0 have very low melting points, whereas the compounds where 1 equals 1 have particularly high clarification points. Thus the substances are capable of extending the liquid crystal regions of existence in mixtures upwardly and downwardly. Other liquid crystal or non-liquid crystal substances, particularly dyes, may be added to the substances according to the invention.

DETAILED DESCRIPTION OF PREFERRED EMBODIMENTS

It was determined how to prepare the new liquid crystalline 4-[trans-4-n-alkylcyclohexanoyloxy]-trans-n-alkylcyclohexanes or 4-[trans-4-n-alkylcyclohexanoyloxy]-3-subst.-benzoyloxy-[trans-4-n-alkylcyclohexane]s.

It was found that 4-[trans-4-n-alkylcyclohexanoyloxy]-trans-n-alkylcyclohexanes or 4-[trans-4-n-alkylcyclohexanoyloxy]-3-subst.-benzoyloxy-[trans-4-n-alkylcyclohexane]s may be prepared by esterification of trans-4-alkylcyclohexane carboxylic acid chlorides or 4-[trans-4-alkylcyclohexanoyloxy]-3-subst.-benzoic acid chlorides with trans-4-alkylcyclohexanols respectively, in a dry organic base, preferably pyridine or quinoline at temperatures between 0° and 60° C., preferably at room temperature, according to the following general scheme:

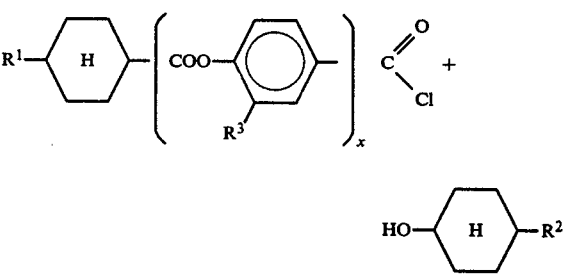

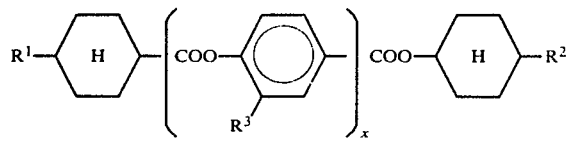

where $R^1 = C_nH_{2n+1}$, $R^2 = C_mH_{2m+1}$, $R^3 = H$, $CH_3, C_2H_5, Cl, Br$ and $X = 0, 1$ and $m, n$ = numbers from 1 to 10.

The following eleven examples will serve to explain the invention:

EXAMPLE 1

Table 1 gives examples for substances where 1 equals 0 together with their transition temperatures. K = crystalline-solid stage; S = smectic; N = nematic; I = isotrope-liquid.

TABLE 1

| No. | $R^1$ | $R^2$ | K | S | H | I |
|---|---|---|---|---|---|---|
| 1/1 | n-C$_4$H$_9$ | n-C$_3$H$_7$ | . | | . | . |
| 1/2 | n-C$_5$H$_{11}$ | n-C$_3$H$_7$ | .23–24 | .37.5 | .52.6 | . |
| 1/3 | CH$_3$ | n-C$_4$H$_9$ | . | | . | . |
| 1/4 | C$_2$H$_5$ | n-C$_4$H$_9$ | .10 | .18 | — | . |
| 1/5 | n-C$_3$H$_7$ | n-C$_4$H$_9$ | .8–10 | .33.5 | .39 | . |
| 1/6 | n-C$_4$H$_9$ | n-C$_4$H$_9$ | .26–27 | .48 | — | . |
| 1/7 | n-C$_5$H$_{11}$ | n-C$_4$H$_9$ | .25.0 | .57–58 | — | . |
| 1/8 | n-C$_6$H$_{13}$ | n-C$_4$H$_9$ | .18–20 | .60–61 | — | . |
| 1/9 | n-C$_7$H$_{15}$ | n-C$_4$H$_9$ | .14–16 | .65–66 | — | . |
| 1/10 | n-C$_8$H$_{17}$ | n-C$_4$H$_9$ | .32 | 69.5 | — | . |
| 1/11 | CH$_3$ | n-C$_5$H$_{11}$ | . | | . | . |
| 1/12 | C$_2$H$_5$ | n-C$_5$H$_{11}$ | .20–21 | .35 | — | . |
| 1/13 | n-C$_3$H$_7$ | n-C$_5$H$_{11}$ | .24 | .51.5 | .54 | . |
| 1/14 | n-C$_4$H$_9$ | n-C$_5$H$_{11}$ | .20–21 | .62.0 | — | . |
| 1/15 | n-C$_5$H$_{11}$ | n-C$_5$H$_{11}$ | .52 | .72.0 | — | . |
| 1/16 | n-C$_6$H$_{13}$ | n-C$_5$H$_{11}$ | .26 | .75.5 | — | . |
| 1/17 | n-C$_7$H$_{15}$ | n-C$_5$H$_{11}$ | .27 | .78.5 | — | . |
| 1/18 | n-C$_8$H$_{17}$ | n-C$_5$H$_{11}$ | . | | . | . |

EXAMPLE 2

Table 2 gives examples for substances where 1 = 1.

TABLE 2

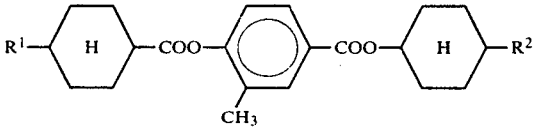

| R | $R^1$ | $R^2$ | K | N | I |
|---|---|---|---|---|---|
| 2/1 | C$_2$H$_5$ | CH$_3$ | .78 | .129 | . |
| 2/2 | C$_2$H$_5$ | C$_4$H$_9$ | .62 | .162 | . |
| 2/3 | C$_2$H$_5$ | C$_5$H$_{11}$ | .59 | .163 | . |
| 2/4 | C$_4$H$_9$ | C$_4$H$_9$ | .72 | .174 | . |
| 2/5 | C$_4$H$_9$ | C$_5$H$_{11}$ | .68 | .182 | . |

EXAMPLE 3

Table 3 gives examples for substances with 1 = 1, R = CH$_3$.

| $R^1$ | $R^2$ | K | H | I |
|---|---|---|---|---|
| C$_2$H$_5$ | C$_5$H$_{13}$ | .53 | .163 | . |
| C$_4$H$_9$ | C$_4$H$_9$ | .75 | .175 | . |

EXAMPLE 4

Mixtures of propylcyclohexanecarboxylic acid butylcyclobutylester (compound 1/5) and pentylcyclohexanecarboxylic acid 4-cyanophenylester possess the transformation temperatures shown in table 4.

TABLE 4

| compd 1/5 | mp° | N/S$_B$ smectic (a) temp dwnwds from (b) temp upwds to | clp. | time for crystallization at −15° C. |
|---|---|---|---|---|
| 1 | 2 | 3 | 4 | 5 |
| 70 | 14–19 | (a) 19.5 (b) 22.5 | 43.7–44.0 | 80 min |
| 60 | 13–30 | (a) 6.5 (b) 11.5 | 47.8–48.0 | 20 min |
| 50 | 18–33 | (a) 12.5 (b) 16 | 51.5–52.8 | 5 min. |
| 40 | 17–36.5 | — | 56.3–58.0 | 5 min |

Cooling speed for all compounds for crystallizing: 4°/min. The 50 mol % mixture shows following electrooptical properties:

| swelling potential: | $U = 1.61$ V; $U_{90\%} = 3.3$ V |
|---|---|
| twist cell: | $f = 500$ Hz; $\theta = 24°$ C. |

TABLE 5

| Rise and decay times | | |
|---|---|---|
| twist cell: | $f = 500$ Hz $\theta = 23°$ C. | |
| thickness of layer: | 23 mu | |
| U/V | rise time 50%/ms | decay time 90%/ms |
| 13.2 | 1360 | 550 |
| 6.5 | 275 | 560 |
| 9.7 | 110 | 570 |
| 14.6 | 40 | 660 |

EXAMPLE 5

The substance M ⅔ has an absorption maximum at $\lambda = 236.3$ nm, the analogous aromatic substance $\lambda 250$ nm. This hypochromic displacement is very advantageous for spectroscopical use of the material because its scale range is increased.

EXAMPLE 6

Preparation of the trans-4-n-alkylcyclohexanols

The compound is prepared by hydrogenation of 4-n-alkylphenols and subsequent separation of the cis/trans isomer mixture.

(a) Hydrogenation of the 4-n-alkylphenols

A solution of 75 g (0.5 mol) 4-n-butylphenol in 200 ml ethanol abs. are shaken in an autoclave at 160° C. and 120 atmospheres pressure hydrogen (measured at RT).

Shaking is conducted until after one to one and a half hours, the calculated pressure drop occurs. The catalyst is filtered off, the solvent vacuumed off, and the resulting compound is fractioned in a water jet vacuum in order to remove unhydrogenated and partially hydrogenated components. Yield=90% of theoretical. All other alkylphenols are prepared by the same method.

R—⟨H⟩—OH

| R | Boiling Point | at mm Hg |
|---|---|---|
| $CH_3$ | 173 | 745 |
| $C_4H_9$ | 114 | 11 |
| $C_5H_{11}$ | 131 | 17 |

(b) Separation of cis- and trans-4-n-alkylcyclohexanols

Variant 1

To 78 g (0.5 mol) of the mixed isomers of 4-n-butylcyclohexanol, obtained by hydrogenation in pyridine an equimolar amount of dinitrobenzoylchloride is added while stirring and cooling in ice. The mixture is boiled 1½ hours upon a water bath and left standing overnight. The mixture is poured upon ice and acidified with concentrated sulphuric acid. The drawn-off product is washed with a dilute solution of sodium bicarbonate, water, dilute hydrochloric acid and again with water. The pure trans-4-n-alkylcyclohexylester is obtained by recrystallization in methanol until the melting point remains consent (approximately 5 times).

3,5-dinitrobenzoic acid trans-4-methylcyclohexyl ester mp=141° C.

3,5-dinitrobenzoic acid trans-4-n-butylcyclohexyl ester mp=115° C.

The respective alcohol is isolated by water vapor distillation and fractioned after saponification of the trans-4-n-alkylcyclohexyl ester with 20% methanolic KOH.

Yield: 25% of theoretical
trans-4-methylcyclohexanol: bp=78° C./12 mm Hg
trans-4-butylcyclohexanol: bp=107° C./9 mm Hg Variant 2

Fractionated distillation on a column packed with twisted bands was the most efficient and rational method for separating the isomers of the 4-n-alkylcyclohexanols. The column had 55 theoretical trays. At a reflux ratio of 1:250 and a column load of 1 ml/min, 50 drops per minute could be removed. Combination of boiling points of 4-n-alkylcyclohexanols when distilling at the twisted band column.

| temperature in °C. | pressure in Torrs | correlation of stereo-isomers (by H—NMR—spectroscopy) |
|---|---|---|
| 4-n-Butylcyclohexanol: | | |
| 61 | 0.35 | cis |
| 64.5 | 0.38 | Isomer mixture ca. 50:50 (estimated) |
| 69.5–70 | 0.45 | trans |
| 4-n-Amylcyclohexanol: | | |
| 77.5 | 0.8 | cis |
| 80–80.5 | 0.7 | Isomer mixture ca. 50:50 (estimated) |
| 85 | 0.85 | trans |

This method of isomer separation resulted in the preparation of larger amounts of pure isomers Proof for purity of stereo-isomers was found by $^1$H-NMR-spectroscopy.

EXAMPLE 7

Preparation of 4-[trans-4-n-alkylcyclohexanoyloxy]-3-subst.-benzoic acid chlorides These compounds are prepared in three steps as follows:

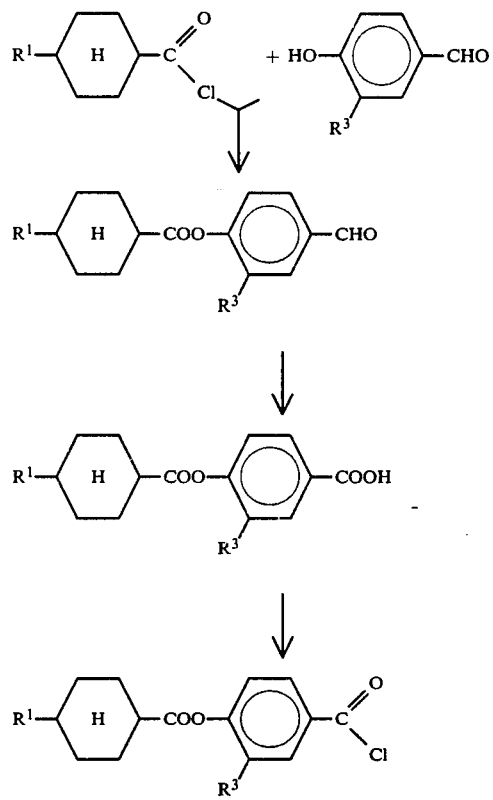

Preparation of 4-[trans-4-n-butylcyclohexanoyloxy]-benzaldehyde (a) 12.2 g (0.1 mol) 4-hydroxybenzaldehyde is dissolved in 150 ml acetone containing 50 ml 2n sodium hydroxide. A solution of 20.3 g (0.1 mol) trans-4-n-butylcyclohexane carboxylic acid chloride in 50 ml acetone is added by drops to the above at room temperature. After two hours, 350 ml water are added, thereby precipitating the substituted benzaldehyde. The resulting raw product is used without any purification.

(b) Preparation of 4-[trans-4-n-butylcyclohexanoyloxy]-benzoic acid

The resulting impure substituted benzaldehyde is dissolved in 70 ml 90% acetic acid. 38 ml 60% acetic acid containing 19 g $CrO_3$ are added to above solution drop by drop at room temperature. After twelve hours stirring at 40° C., 200 ml water are added. The precipitated substituted benzoic acid is sucked off, dried and crystallized in an ethanol-methanol mixture. Yield=80% of theoretical.

(c) Preparation of 4-[trans-4-n-butylcyclohexanoyloxy]-benzoylchloride 20 ml purified thionyl chloride and three drops pyridine are added to 1.52 g (0.005 mol) 4-[trans-4-n-butylcyclohexanoyloxy]-benzoic acid. The mixture is boiled 5 hours upon a water bath. Thereafter excess thionyl chloride is completely distilled off under vacuum, while upon the water bath. The remaining acid chloride may be used for esterification without further purification. The substituted benzyl chlorides with other alkyl substituents are prepared by the same method by using respective trans-4-n-alkylcyclohexane carboxylic acid chlorides. 4-[trans-4-n-alkylcyclohexanoyloxy]-benzoic acids

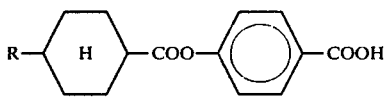

| R | K | N | I |
|---|---|---|---|
| $C_2H_5$ | .220-224 | .226-229 | . |
| $C_4H_9$ | .215-220 | .230-235 | . |
| $C_6H_{13}$ | .212-215 | .227-232 | . |

K = crystalline-solid
N = nematic
I = isotropic-liquid

EXAMPLE 8

Preparation of 4-[trans-butylcyclohexanoyloxy]-trans-n-butylcyclohexane 2 g (0.01 mol) trans-4-n-butylcyclohexane carboxylic acid chloride are added drop by drop to 1.6 g (0.01 mol) trans-4-n-butylcyclohexanol in 30 ml dry pyridine. The solution is shaken until pyridinium hydrochloride precipitates, left standing overnight and heated one hour to 60° C. upon a water bath thereafter. After cooling, the mixture is poured upon ice which contains 20 ml concentrated sulfuric acid. The ester is dispersed in ether and washed with a dilute solution of sodium bicarbonate, water, dilute hydrochloric acid and again with water. It is dissolved in hot methanol and carefully precipitated by freezing in an ice bath.

This procedure is repeated twice. Yield: 65% of theoretical

EXAMPLE 9

All 4-[trans-alkylcyclohexanoyloxy]-trans-n-alkylcyclohexanes may be prepared according to the method in Example 8. Table 1 gives examples for these substances.

EXAMPLE 10

4-[trans-4-n-butylcyclohexanoyloxy]-benzoic acid-[trans-4-n-butylcyclohexylester] 1.6 g (0.01 mol) trans-4-n-butylcyclohexanol, dissolved in 40 ml dry pyridine, are added to 3.3 (0.01 mol) 4-[trans-4-n-butylcyclohexanoyloxy-]benzoyl chloride. The mixture is shaken until the solution is clear and ultimately pyridinium hydrochloride precipitates. The mixture is heated to 60° C. upon the water bath after standing overnight. After cooling, it is poured over ice and 13 ml concentrated sulphuric acid. The solids are sucked off, washed with water several times, and dried. The ester is purified by recrystallizing three times from methanol. Yield = 80% of theoretical.

TABLE 1

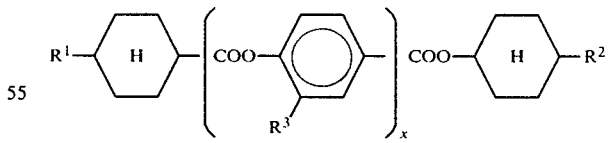

| No. | $R^1$ | $R^2$ | K | S | N | I |
|---|---|---|---|---|---|---|
| 1/1 | n-$C_4H_9$ | n-$C_3H_7$ | .<10 | .20 | .38 | . |
| 1/2 | n-$C_5H_{11}$ | n-$C_3H_7$ | .23-24 | .37.5 | .52,5 | . |
| 1/3 | $C_2H_5$ | n-$C_4H_9$ | .10 | .18 | — | . |
| 1/4 | n-$C_3H_7$ | n-$C_4H_9$ | .8-10 | .33,5 | −39 | . |
| 1/5 | n-$C_4H_9$ | n-$C_4H_9$ | .26-27 | .48 | — | . |
| 1/6 | n-$C_5H_{11}$ | n-$C_4H_9$ | .25.0 | .57-58 | — | . |
| 1/7 | n-$C_6H_{13}$ | n-$C_4H_9$ | .18-20 | .60-61 | — | . |
| 1/8 | n-$C_7H_{15}$ | n-$C_4H_9$ | .14-16 | .65-66 | — | . |
| 1/9 | n-$C_8H_{17}$ | n-$C_4H_9$ | .32 | .69.5 | — | . |
| 1/10 | $C_2H_5$ | n-$C_5H_{11}$ | .20-21 | .35 | — | . |
| 1/11 | n-$C_3H_7$ | n-$C_5H_{11}$ | .24 | .51.5 | .54 | . |
| 1/12 | n-$C_4H_9$ | n-$C_5H_{11}$ | .20-24 | .62.0 | — | . |
| 1/13 | n-$C_5H_{11}$ | n-$C_5H_{11}$ | .52 | .72.0 | — | . |
| 1/14 | n-$C_6H_{13}$ | n-$C_5H_{11}$ | .26 | .75.5 | — | . |
| 1/15 | n-$C_7H_{15}$ | n-$C_5H_{11}$ | .27 | .78.5 | — | . |

TABLE 2

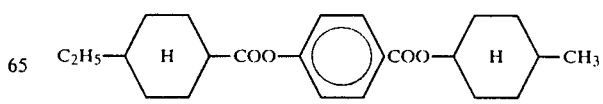

| R | $R^1$ | $R^2$ | K | N | I |
|---|---|---|---|---|---|
| 2/1 | $C_2H_5$ | $CH_3$ | .78 | .129 | . |
| 2/2 | $C_2H_5$ | $C_4H_9$ | .62 | .162 | . |
| 2/3 | $C_2H_5$ | $C_5H_{11}$ | .59 | .163 | . |
| 2/4 | $C_4H_9$ | $C_4H_9$ | .72 | .174 | . |
| 2/5 | $C_4H_9$ | $C_5H_{11}$ | .68 | .182 | . |

EXAMPLE 11

All 4-[trans-4-n-alkylcyclohexanoyloxy]-3-subst.-benzoyloxy-[trans-4-n-alkylcyclohexane]s are synthesized analogous to Example 10 by using the respective alkylcyclohexanols and substituted benzoylchlorides. Table 2 shows examples for these substances.

We claim:

1. Liquid crystal 4-trans-4-n-alkylcyclohexanoyloxy-trans-n-alkyl-cyclohexanes and/or 4-trans-4-n-alkylcyclohexanoyloxy-3-subst.-benzoyloxy-trans-4-n-alkylcyclohexanes respectively having the general formula where $R^1 = C_nH_{2n+1}$; $R^2 = C_mH_{2m+1}$; $R^3 = H$, $CH_3$, $CH_2H_5$, Cl, Br and X = 1; m, n = 1 to 10.

2. The liquid crystal according to claim 1 which is

3. The liquid crystal according to claim 1 which is

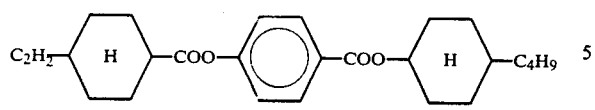
4. The liquid crystal according to claim 1 which is
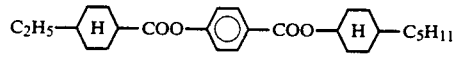
5. The liquid crystal according to claim 1 which is
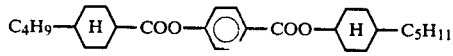
6. The liquid crystal according to claim 1 which is
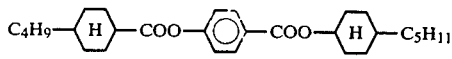
7. The liquid crystal according to claim 1 which is
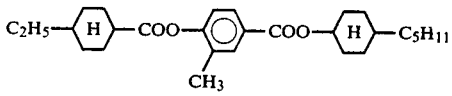
8. The liquid crystal according to claim 1 which is
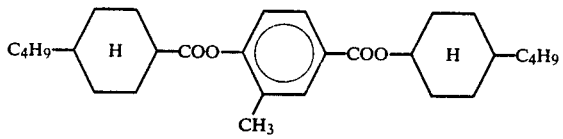
9. A liquid crystalline mixture comprising liquid crystal subst.-benzolyloxy-trans-4-n-alkylcyclohexanes according to claim 1.
* * * * *